United States Patent
Matsuoka et al.

(10) Patent No.: US 9,295,747 B2
(45) Date of Patent: Mar. 29, 2016

(54) CONTACT LENS CARE PREPARATION AND PACKAGING SOLUTION

(75) Inventors: Yosuke Matsuoka, Tsukuba (JP); Norio Iwakiri, Tsukuba (JP); Mao Maruhashi, Tsukuba (JP); Nobuyuki Sakamoto, Tsukuba (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 14/381,870

(22) PCT Filed: Mar. 2, 2012

(86) PCT No.: PCT/JP2012/055378
§ 371 (c)(1),
(2), (4) Date: Aug. 28, 2014

(87) PCT Pub. No.: WO2013/128633
PCT Pub. Date: Sep. 6, 2013

(65) Prior Publication Data
US 2015/0024987 A1    Jan. 22, 2015

(51) Int. Cl.
*C11D 3/37* (2006.01)
*A61L 12/10* (2006.01)
*A61L 12/08* (2006.01)
*A61L 12/14* (2006.01)
*C11D 3/00* (2006.01)

(52) U.S. Cl.
CPC ............... *A61L 12/10* (2013.01); *A61L 12/08* (2013.01); *A61L 12/14* (2013.01); *C11D 3/0078* (2013.01); *C11D 3/3719* (2013.01); *C11D 3/3765* (2013.01); *C11D 3/3773* (2013.01); *C11D 3/3784* (2013.01)

(58) Field of Classification Search
CPC .. C11D 3/3719; C11D 3/3765; C11D 3/3773; C11D 3/3784; A61L 12/08; A61L 12/14
USPC ......................... 510/112, 475, 504
See application file for complete search history.

(56) References Cited

U.S. PATENT DOCUMENTS

| | | | |
|---|---|---|---|
| 8,680,314 B2 * | 3/2014 | Yoshioka et al. | 558/172 |
| 2003/0086957 A1 | 5/2003 | Hughes et al. | |
| 2003/0186825 A1 | 10/2003 | Mitani et al. | |
| 2004/0197585 A1 | 10/2004 | Hughes et al. | |
| 2008/0314767 A1 | 12/2008 | Lai et al. | |
| 2009/0100801 A1 | 4/2009 | Zhao et al. | |
| 2013/0310591 A1 * | 11/2013 | Yoshioka et al. | 558/145 |

FOREIGN PATENT DOCUMENTS

| | | |
|---|---|---|
| JP | 11-29800 A | 2/1999 |
| JP | 2000-147442 A | 5/2000 |
| JP | 2003-005136 A | 1/2003 |
| JP | 2003-520107 A | 7/2003 |
| JP | 2012-088524 A | 5/2012 |
| JP | 2012-088525 A | 5/2012 |
| WO | 02/15911 A1 | 2/2002 |

OTHER PUBLICATIONS

James Lonnen et al., "Disinfection Efficacy and Encystment Rate of Soft Contact Lens Multipurpose Solutions Against Acanthamoeba," Eyes & Contact Lens, Jan. 2010, pp. 26-32, vol. 36, No. 1.
International Searching Authority, International Search Report of PCT/JP2012/055378 dated Jun. 12, 2012.

* cited by examiner

*Primary Examiner* — Gregory R Delcotto
(74) *Attorney, Agent, or Firm* — Sughrue Mion, PLLC

(57) ABSTRACT

Provided are a contact lens care preparation capable of imparting durable surface lubricity and amebic adhesion inhibitory effect to a contact lens surface through a simple treatment, and a contact lens packaging solution utilizing the same. The contact lens care preparation is composed of a solution containing 0.01 to 2 weight/volume % of a polymer having particular monomer units with a phosphorylcholine-like group, particular (meth)acrylamide derivative units, and particular monomer units with a hydrophobic group at a particular ratio, and a weight average molecular weight of 5,000 to 2,000,000, and is useful as a contact lens packaging solution.

2 Claims, No Drawings

CONTACT LENS CARE PREPARATION AND PACKAGING SOLUTION

CROSS REFERENCE TO RELATED APPLICATIONS

This is a National Stage of International Application No. PCT/JP2012/055378 filed Mar. 2, 2012, the contents of which are incorporated herein by reference in its entirety.

FIELD OF ART

The present invention relates to a contact lens care preparation capable of imparting durable surface lubricity and amebic adhesion inhibitory effect to contact lens surfaces through a simple treatment, and a packaging solution for use in hermetically packaging a contact lens in a container.

BACKGROUND ART

Attempts have recently been made, for the purpose of improving comfort in wearing soft contact lenses, to add a polymer that improves lens surface lubricity, to soft contact lens care preparations and packaging solutions. With such a conventionally proposed polymer, however, the improvement lasts only insufficiently and, in particular, the wearing comfort is impaired when the lenses are worn throughout the day, so that further improvement is desired.

Commercially-available lens care preparations used for storing soft contact lenses are usually disinfectant for preventing proliferation of bacteria and ameba during storage. As disclosed in Non-patent Publication 1, however, such preparations are not actually effective for ameba, and infections caused by amebic adhesion have been social concerns, to which sufficient solutions are yet to be found. This is because the soft contact lenses are made of hydrogel, to which surface functionalities, such as lubricity and inhibition of amebic adhesion, are hard to be imparted with durability through a simple process.

Polymers having a phosphorylcholine-like group are known to have excellent biocompatibilities, such as blood compatibility, ability to inactivate complements, and nonadsorbability of biomaterials, due to their phospholipid-like structure derived from biomembranes, and also have various excellent properties, such as extremely high hydrophilicity and moisture-retaining property. In view of this, researches have actively been made concerning synthesis and applications of polymers having a phosphorylcholine-like group for the purpose of development of biomaterials.

For example, Patent Publication 1 proposes to use a polymer obtained by polymerization of a monomer having a phosphorylcholine group and a monomer having a hydrophobic alkyl group, in a contact lens wetting solution.

However, this polymer has a problem of insufficient lubrication, and has not been investigated for amebic adhesion inhibitory effect, which is in fact revealed to be insufficient.

Patent Publication 2 proposes a copolymer of a monomer having a phosphorylcholine group and another hydrophilic monomer. This copolymer, however, is highly hydrophilic, so that it is discharged with lacrimal fluid while the lenses are worn, and hard to be sustained sufficiently.

Patent Publication 3 discloses addition of a copolymer of a monomer having a phosphorylcholine group and butylmethacrylate to a contact lens packaging solution. However, the butyl group in the copolymer has weaker coagulation power compared to a long chain alkyl group, and causes less change in finger feel in an aqueous solution, so that sufficient improvement in lens wearing comfort is not achieved.

Patent Publication 4 discloses achievement of excellent cleansing power by using a copolymer of a monomer having a phosphorylcholine group and alkylmethacrylate in a contact lens cleansing solution. However, the copolymer has not been investigated for capability of imparting lens surface lubricity or amebic adhesion inhibitory effect, which are in fact revealed to be insufficient.

Patent Publication 1: WO 02/15911 A1

Patent Publication 2: US 2008/0314767 A1

Patent Publication 3: US 2009/0100801 A1

Patent Publication 4: JP 2003-005136-A

Non-patent Publication 1: Eye & Contact Lens 36(1), p 26-32 (2010)

SUMMARY OF THE INVENTION

It is an object of the present invention to provide a contact lens care preparation capable of imparting durable surface lubricity and amebic adhesion inhibitory effect to a contact lens surface through a simple treatment.

It is another object of the present invention to provide a contact lens packaging solution capable of imparting durable surface lubricity and amebic adhesion inhibitory effect to a contact lens surface.

The present inventors have made intensive researches in view of the above objects to find out that a copolymer obtained by polymerization of a particular monomer having a phosphorylcholine-like group, a (meth)acrylamide derivative, and a monomer having a hydrophobic group, may be used as a material having particularly excellent surface lubrication and amebic adhesion inhibitory effect, to thereby achieve the present invention.

According to the present invention, there is provided a contact lens care preparation consisting of a solution comprising 0.01 to 2.0 weight/volume % of a polymer having structural units represented by formulae (1a) to (1c):

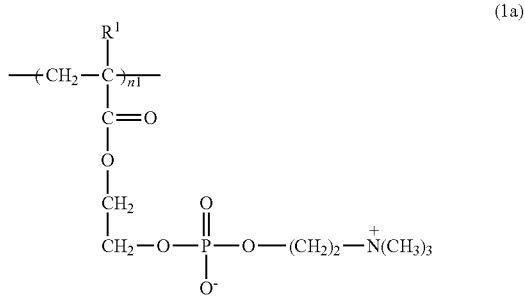

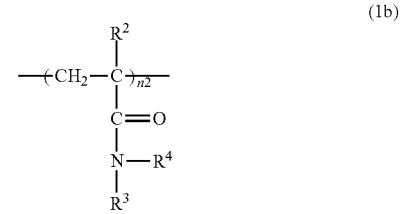

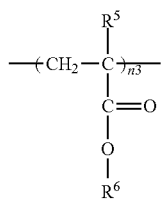

wherein $R^1$, $R^2$ and $R^5$ are each independently a hydrogen atom or a methyl group; $R^3$ and $R^4$ are each independently a methyl or ethyl group; $R^6$ is a monovalent hydrocarbon group having 12 to 24 carbon atoms; n1, n2, and n3 represent a molar ratio of the structural units, and fulfill n1:n2:n3=100:10 to 400:2 to 50,
and a weight average molecular weight of 5,000 to 2,000,000 (sometimes referred to as PC polymer hereinbelow) (sometimes referred to as the present care preparation hereinbelow).

According to the present invention, there is also provided a contact lens packaging solution consisting of the contact lens care preparation mentioned above (sometimes referred to as the present packaging solution hereinbelow).

According to the present invention, there is further provided a contact lens package comprising an unused contact lens and the present packaging solution, contained and sealed in a container having a storage space of the contact lens and a storage space of the present packaging solution.

According to the present invention, there is also provided use of the PC polymer for the manufacture of a contact lens packaging solution.

The present care preparation, which contains the PC polymer having at a particular ratio particular monomer units with a phosphorylcholine-like group, (meth)acrylamide derivative units, and monomer units with a hydrophobic group, and the PC polymer having biocompatibility, hydrophilicity, and gel-forming property, is capable of imparting durable surface lubricity and amebic adhesion inhibitory effect to contact lens surfaces through a simple treatment. The present care preparation may suitably be used as a packaging solution for use in sealingly packaging a contact lens, such as soft contact lenses, in a container.

PREFERRED EMBODIMENTS OF THE INVENTION

The present invention will now be explained in detail.

The PC polymer used in the present care preparation has structural units represented by above formulae (1a) to (1c) and a weight average molecular weight of 5,000 to 2,000,000, preferably 100,000 to 1,500,000. With a weight average molecular weight of less than 5,000, the adhesion of the PC polymer to contact lens surfaces may not be sufficient, resulting in inferior durability, whereas with over 2,000,000, the viscosity of the PC polymer during manufacture may be too high, which leads to difficulties in handling.

The PC polymer may optionally have structural units other than those represented by the formulae (1a) to (1c) as long as the effects of the present invention are not impaired.

In the formulae (1a) to (1c) constituting the PC polymer, $R^1$, $R^2$ and $R^5$ are each independently a hydrogen atom or a methyl group. $R^3$ and $R^4$ are each independently a methyl or ethyl group. $R^6$ is a monovalent hydrocarbon group having 12 to 24 carbon atoms, for example, a lauryl, stearyl, or behenyl group.

In the formulae (1a) to (1c), n1, n2, and n3 represent the molar ratio of the structural units, and fulfill n1:n2:n3=100:10 to 400:2 to 50. When n2 is more than 400, sufficient biocompatibility may not be attained, whereas when less than 10, improvement in lens wearing comfort may be difficult. When n3 is less than 2, physically-crosslinked-gel-forming property through hydrophobic interaction is poor, which lowers adhesion to contact lens surfaces and may not result in lasting improvement in lens wearing comfort. When n3 is more than 50, the hydrophilicity of the PC polymer is low, which may cause low solubility in an aqueous solution and low ability of surface hydrophilization.

The PC polymer may be prepared, for example, by radical polymerization of a monomer composition containing a monomer having a phosphorylcholine-like group represented by formula (2):

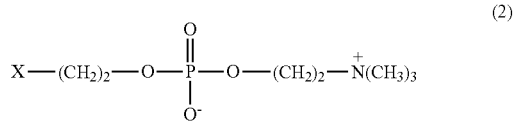

(referred to as PC monomer hereinbelow), a (meth)acrylamide represented by formula (3):

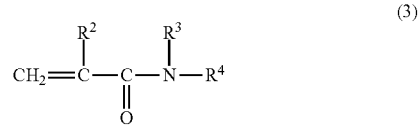

or a derivative thereof, and a monomer having a hydrophobic group represented by formula (4):

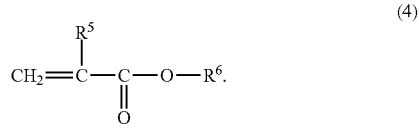

The monomer composition may optionally contain other polymerizable monomers in addition to the above-mentioned monomers.

In formula (2), X is a monovalent organic group having a polymerizable functional group with an unsaturated bond.

In formulae (3) and (4), $R^2$ to $R^6$ are the same groups or atoms as in formulae (1b) and (1c).

The PC monomer may preferably be, for example, 2-((meth)acryloyloxy)ethyl-2'-(trimethylammonio)ethylphosphate in view of availability, more preferably 2-(methacryloyloxy)ethyl-2'-(trimethylammonio)ethylphosphate represented by formula (5):

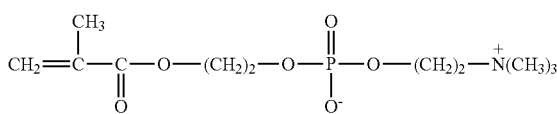

(referred to as MPC hereinbelow).

The PC monomer may be prepared by a known method, for example, by reaction of a polymerizable monomer having a hydroxyl group and 2-bromoethylphosphoryl dichloride in the presence of a tertiary base, followed by further reaction with a tertiary amine as disclosed in JP-S54-63025-A, or by reaction of a polymerizable monomer having a hydroxyl group and a cyclic phosphorus compound to obtain a cyclic compound, which in turn is subjected to ring-opening reaction with a tertiary amine as disclosed in JP-S58-154591-A.

The (meth)acrylamide represented by formula (3) or a derivative thereof may preferably be, for example, N,N-dimethyl(meth)acrylamide, N,N-diethyl(meth)acrylamide, or N-acryloylmorpholine.

The hydrophobic monomer represented by formula (4) may be, for example, a straight alkyl(meth)acrylate, such as lauryl(meth)acrylate, stearyl(meth)acrylate, or behenylmethacrylate.

Examples of the other polymerizable monomers optionally used in the monomer composition may include a straight or branched alkyl(meth)acrylate such as methyl(meth)acrylate, ethyl(meth)acrylate, butyl(meth)acrylate, or 2-ethylhexyl (meth)acrylate; a cyclic alkyl(meth)acrylate such as cyclohexyl(meth)acrylate; a (meth)acrylate having an aromatic group such as benzyl(meth)acrylate or phenoxyethyl(meth)acrylate; a styrene monomer such as styrene, methylstyrene, or chloromethylstyrene; a vinyl ether monomer such as methylvinyl ether or butylvinyl ether; a vinyl ester monomer such as vinyl acetate or vinyl propionate; a hydrophilic (meth)acrylate having a hydroxyl group such as polyethylene glycol (meth)acrylate, polypropylene glycol (meth)acrylate, N-vinylpyrrolidone, 2-hydroxyethyl(meth)acrylate, 2-hydroxybutyl(meth)acrylate, or 4-hydroxybutyl(meth)acrylate; a monomer having an acid radical such as (meth)acrylic acid, styrenesulfonic acid or (meth)acryloyloxy sulfonic acid; a monomer having an amino group such as aminoethylmethacrylate, dimethylaminoethyl(meth)acrylate, or N,N-dimethylaminopropyl(meth)acrylamide; and a monomer having a cationic group such as 2-hydroxy-3-(meth)acryloyloxypropyltrimethylammonium chloride.

Some of the other polymerizable monomers may affect the adhesion of the PC polymer to contact lens surfaces, so that such other monomers are preferably selected taking their characteristics into account. In view of expression of biocompatibility and lens surface adhesion of the resulting PC polymer, among the other polymerizable monomers, a monomer having a hydroxyalkyl group, such as 2-hydroxyethyl(meth)acrylate or 2-hydroxybutyl(meth)acrylate, or a monomer having a cationic group, such as (meth)acryloyloxyethyltrimethylammonium chloride or 2-hydroxy-3-(meth)acryloyloxypropyltrimethylammonium chloride is preferred.

The content of the other polymerizable monomers, when contained, in the monomer composition for the preparation of the PC polymer may suitably be selected so as not to affect the effects of the present invention, and may preferably be not more than 50 in molar ratio with respect to n1 being 100 in formula (1a) constituting the PC polymer.

The PC polymer may be prepared by a known method, for example, radical polymerization, such as bulk, suspension, emulsion, or solution polymerization, of the monomer composition in the presence of a radical polymerization initiator in an atmosphere of or substituted with an inert gas, such as nitrogen, carbon dioxide, argon, or helium. Among these, solution polymerization is preferred in the light of purification. Purification of the PC polymer may be effected by a common method, such as re-precipitation, dialysis, or ultrafiltration.

The radical polymerization initiator may be, for example, an azo radical polymerization initiator, such as 2,2-azobis(2-diaminopropyl)dihydrochloride, 2,2-azobis(2-(5-methyl-2-imidazoline-2-yl)propane)dihydrochloride, 4,4-azobis(4-cyanovaleric acid), 2,2-azobisisobutylamide dihydrate, 2,2-azobis(2,4-dimethylvaleronitrile), or 2,2-azobisisobutylonitrile (AIBN); an organic peroxide, such as benzoyl peroxide, diisopropyl peroxydicarbonate, t-butylperoxy-2-ethylhexanoate, t-butyl peroxypivalate, t-butyl peroxydiisobutyrate, lauroyl peroxide, t-butyl peroxyneodecanoate, or succinyl peroxide; or a persulfate, such as ammonium persulfate, potassium persulfate, or sodium persulfate. One or a mixture of these radical polymerization initiators may be used. The amount of the polymerization initiator to be used may usually be 0.001 to 10 parts by mass, preferably 0.01 to 5.0 parts by mass with respect to 100 parts by mass of the monomer composition.

The PC polymer may be prepared in the presence of a solvent which dissolves but does not react with the monomer composition. Examples of the solvent may include water; alcohol solvents, such as methanol, ethanol, n-propanol, or isopropanol; ketone solvents, such as acetone, methyl ethyl ketone, or diethyl ketone; ester solvents such as ethyl acetate; straight or cyclic ether solvents, such as ethyl cellosolve, tetrahydrofuran, or N-methylpyrrolidone, and nitrogen-containing solvents, such as acetonitrile or nitromethane. The solvent may preferably be water, alcohol, or a mixture thereof.

The present care preparation may be prepared by dissolving the PC polymer in water, alcohol, such as methanol, ethanol, or isopropanol, or a mixture thereof at 0.01 to 2.0 weight/volume % (abbreviated as w/v % hereinbelow). At a PC polymer concentration of less than 0.01 w/v %, the amebic adhesion inhibitory effect or the lubricating effect may not be sufficient, whereas at over 2.0 w/v %, the solution viscosity may be too high.

The present care preparation may optionally contain a buffer for pH adjustment, such as citric acid, citrate, boric acid, borate, phosphoric acid, phosphate, tris(hydroxymethyl)aminomethane hydrochloride, or a mixture of two or more of these.

The concentration of the buffer, when contained, in the present care preparation is preferably 0.2 to 1.5 w/v %. At less than 0.2 w/v %, the buffering capacity is too low to control the pH, whereas at over 1.5 w/v %, the buffer may impair the solubility of other components. The pH of a packaging solution used in packaging contact lenses is preferably about 6 to 9, particularly preferably about 7.5, so that the pH of the present care preparation when used as a contact lens packaging solution is preferably adjusted to the above range.

The present care preparation may optionally contain inorganic chlorides, such as sodium chloride, potassium chloride, magnesium chloride, or a mixture of two or more of these; or polyols, such as glycerin or sugars, for the control of osmotic pressure.

The concentration of the inorganic chlorides or the polyols, when contained, in the present care preparation is preferably 0.1 to 1.5 w/v %. At less than 0.1 w/v % or over 1.5 w/v %, deformation of contact lenses or irritation of the eyes may be caused.

The osmotic pressure of the present care preparation is preferably within an ophthalmologically acceptable level, for example, at least about 200 mOsm/kg, preferably about 200 to 400 mOsm/kg.

The present care preparation may optionally contain polymers other than the PC polymer for the adjustment of solution viscosity.

Examples of such polymers may preferably include polyacrylic acid, acrylic acid-alkylmethacrylate copolymers, 2-hydroxyethylmethacrylate-methacrylic acid copolymers, polyanions, polyvinyl alcohols, and polysaccharides, such as hydroxyethyl cellulose, carboxymethylcellulose, chitosan, pullulan, or hyaluronic acid.

The content of the polymers other than the PC polymer, when contained, in the present care preparation may suitably be adjusted for the present care preparation to have a desired viscosity.

The present care preparation may optionally contain other soluble components as necessary other than the above components, for example, a preservative, such as chlorhexidine gluconate, polyhexamethylene biguanide, benzalkonium chloride, paraben, or a mixture of two or more of these.

The concentration of the preservative, when contained, in the present care preparation is preferably less than 0.1 w/v %. At over 0.1 w/v %, the preparation may be too irritative to the eyes.

The present care preparation may be used as it is as a packaging solution of the present invention for use in sealingly packaging contact lenses, such as soft contact lenses, in a container, or also as a component of a contact lens wetting solution or eye drops.

As used herein, the packaging solution is a solution that is sealed in a packaging container, such as a blister package, together with a contact lens. In general, soft contact lenses are swollen with an aqueous solution before use, so that the lenses are already swollen with an aqueous solution before factory shipment and sealed in a packaging container readily for use.

The care preparation and the packaging solution according to the present invention are capable of hydrophilizing and highly lubricating contact lens surfaces by contact therewith, and have an effect of reducing physical discomfort upon and during wearing of contact lenses. The preparation and the solution are also capable of maintaining surface lubricity and imparting amebic adhesion inhibitory effect.

The care preparation and the packaging solution according to the present invention are not intended for a specific kind of contact lenses, but are particularly useful with soft contact lenses. Examples of soft contact lenses may include conventional hydrogel lenses produced by polymerization of 2-hydroxyethylmethacrylate or methacrylic acid/2-hydroxyethylmethacrylate followed by swelling with an aqueous solution; and silicon hydrogel lenses produced by copolymerization of a hydrophilic monomer, such as 2-hydroxyethylmethacrylate, N-vinylpyrrolidone, or N,N-dimethylacrylamide, with a monomer having a siloxanyl group, followed by swelling with an aqueous solution.

The care preparation and the packaging solution according to the present invention are adapted to contact lenses, but also useful in various other fields, such as medical devices, cosmetics, and biochemical analysis, particularly preferably medical devices, which essentially require biocompatibility. Specifically, the preparation and the solution may be expected to be used, for example, for vascular prosthesis, catheters, dialyzers, blood filters, drug delivery vehicles, or wound covering materials.

EXAMPLES

The present invention will now be explained in more detail with reference to Examples, which are not intended to limit the present invention.

Various measurements in Examples were performed as follows.

<Measurement of Molecular Weight>

5 mg of the obtained polymer was dissolved in 1 g of a methanol/chloroform mixed solvent (8/2 by volume) to prepare a sample solution. Other conditions are as follows:

column: PLgel-mixed-C; reference material: polyethylene glycol; detection: differential refractometer RI-8020 (manufactured by TOSOH CORPORATION); calculation of weight average molecular weight (Mw): molecular weight calculation program (GPC program for SC-8020); flow rate: 1 ml/min; sample solution injection volume: 100 μl; column temperature: 40° C.

The number average molecular weight of the polymer was determined by gel permeation chromatography (GPC) with polyethylene glycol as a standard sample. Specifically, the obtained aqueous polymer solution was diluted with distilled water to 0.5 mass %, filtered through a 0.45 μm membrane filter, and subjected to the measurement as a test solution.

For evaluation of surface hydrophilicity, 2-hydroxyethylmethacrylate (HEMA) gel and silicon hydrogel were prepared in the following manner:

Preparation of HEMA Gel

A fluororesin (PTFE) spacer of 1 mm thick was held between polyethylene terephthalate (PET) films, which in turn was held between glass plates, to thereby fabricate a cell for HEMA gel polymerization. 100 parts by mass of HEMA, 0.3 parts by mass of ethylene glycol dimethacrylate, and 0.05 parts by mass of AIBN were mixed, poured into the polymerization cell, and polymerized at 100° C. for 2 hours in a nitrogen atmosphere to obtain a transparent polymerization product. The polymerization product was swollen with ion-exchanged water, and stored in a phosphate buffer solution provided in ISO 18369-3 (referred to as ISO saline hereinbelow).

Preparation of Silicon Hydrogel

A fluororesin (PTFE) spacer of 1 mm thick was held between polyethylene terephthalate (PET) films, which in turn was held between glass plates, to thereby fabricate a cell for silicon hydrogel polymerization. 60 parts by mass of 2-methacryloyloxyethyl=3-[(tristrimethylsiloxy) silyl] propyl=succinate, 20 parts by mass of HEMA, 20 parts by mass of N-vinylpyrrolidone, 0.3 parts by mass of ethylene glycol dimethacrylate, and 0.05 parts by mass of AIBN were mixed, poured into the polymerization cell, and polymerized at 100° C. for 2 hours in a nitrogen atmosphere to obtain a transparent polymerization product. The polymerization product was swollen with ion-exchanged water, and stored in ISO saline.

<Measurement of Surface Friction Coefficient>

The surface friction coefficient of the HEMA gel or the silicon hydrogel was measured in saline three times each, using a friction tester (trade name KES-SE, manufactured by KATO TECH CO., LTD.), and the average of the three measurements was obtained.

Conditions for Treatment with Care Preparation

The HEMA gel or the silicon hydrogel was soaked in the obtained care preparation overnight, and then subjected to the measurement of the surface friction coefficient.

Conditions for Treatment with Packaging Solution

The HEMA gel or the silicon hydrogel was soaked in the obtained packaging solution, autoclaved at 120° C. for 15 minutes, cooled down to the room temperature, and subjected to the measurement of the surface friction coefficient.

Conditions for Measurement with Measuring Device

Sensitivity: H; probe speed: 1 mm/sec; load: 25 g.

Evaluation: evaluation was made according to the following grades with reference to the counterpart with no polymer (Comparative Example 2-1) as will be discussed later:

A: the friction coefficient is less than 1/10;
B: the friction coefficient is not less than 1/10 and less than 1/3;
C: the friction coefficient is not less than 1/3.

<Evaluation of Surface Water-Wettability (Hydrophilicity)>

The same HEMA gel or silicon hydrogel as used in the evaluation of the surface friction coefficient was washed with 100 ml of ISO saline, and soaked in 100 ml of fresh ISO saline. The gel was drawn out of the saline, and the time elapsed until the surface water film was broken was measured. The evaluation was made according to the following grades:

A: the time elapsed until the water film on the gel surface was broken was not less than 30 seconds;
B: the time elapsed until the water film on the gel surface was broken was not less than 10 seconds and less than 30 seconds;
C: the time elapsed until the water film on the gel surface was broken was less than 10 seconds.

<Evaluation of Ability to Inhibit *Acanthamoeba* Adhesion>

Preparation of Lens Sample

SEED 1 DAY FINE UV (trade name, manufactured by SEED CO., LTD.) was thoroughly washed with ISO saline, soaked in the obtained care preparation or packaging solution (sometimes referred to as the polymer solution hereinbelow), and autoclaved at 121° C. for 15 minutes. The sample after cooled was subjected to the measurement.

Preparation of Media

The following reagents were mixed and autoclaved at 121° C. to prepare a PYG liquid medium:

10 g of proteose peptone (manufactured by SIGMA-ALDRICH CORP.), 0.5 g of yeast extract (manufactured by BECTON, DICKINSON AND COMPANY), 4 ml of 0.05 M $CaCl_2$, 5 ml of 0.4 M $MgSO_4 \cdot 7H_2O$, 5 ml of 0.25 M $Na_2HPO_4 \cdot 7H_2O$, 5 ml of 0.25 M $KH_2PO_4$, 5 ml of 0.005 M $Fe(NH_4)_2(SO_4)_2 \cdot 6H_2O$, 25 ml of 2M glucose solution, and 450 ml of ion-exchanged water.

Measurement Method

*Acanthamoeba* was introduced into a culture flask where the PYG liquid medium was placed, and cultured at 25° C. for 3 to 4 days. The cultured *Acanthamoeba* was scraped from the flask bottom with a cell scraper, and the medium was removed in a centrifuge (2000 rpm). Then a phosphate buffer was added to adjust the cell count to about $1 \times 10^7$ cells/ml to prepare an ameba suspension.

In a PP tube, 2 ml of the ameba suspension and one lens were placed, and shake-cultured (150 rpm) at 37° C. for 10 minutes. Here, lenses in two different states, namely under Conditions 1 and 2, were used:

Condition 1: the autoclaved lens was taken out of the polymer solution immediately before the evaluation, and washed with ISO saline before use.

Condition 2: the autoclaved lens was taken out, washed with ISO saline, and left in ISO saline for about 12 hours before use.

The cultured lens was taken out, rinsed with a phosphate buffer to remove excess ameba, and finally placed in a well of a 24-well plate containing 500 μl of a phosphate buffer. In the well containing the lens, 500 μl of ATP extraction reagent (trade name LUCIFER 250 PLUS, manufactured by KIKKOMAN) was added and stirred. The resulting extraction liquid was taken out at 100 μl into a well of a 96-well plate, and 50 μl of ATP measurement reagent (trade name LUCIFER 250 PLUS, manufactured by KIKKOMAN) was added and stirred. After 20 seconds, the strength of luminescence was measured, from which the ameba adhesion inhibitory effect was evaluated according to the grades below.

Using a solution without a polymer to be discussed later, and based on the strength of luminescence under Condition 1 (being 100), the care preparation of Comparative 1-1 and the packaging solution of Comparative Example 2-1 were used as the references.

Evaluation

A: the strength of luminescence was less than 30;
B: the strength of luminescence was not less than 30 and less than 50;
C: the strength of luminescence was not less than 50.

Synthesis Example 1-1

Polymer A-1; MPC 0.50—SMA 0.05—DMAA 0.45

31.75 g of MPC (manufactured by NOF CORPORATION), 3.64 g of stearyl methacrylate (SMA, manufactured by NOF CORPORATION), and 9.60 g of N, N-dimethylacrylamide (DMAA, manufactured by KOHJIN CO., LTD.) were dissolved in 55.0 g of ethanol, placed in a four-neck flask, and bubbled with nitrogen for 30 minutes. Then 0.10 g of PERBUTYL ND (trade name, manufactured by NOF CORPORATION, abbreviated as PB-ND hereinbelow) was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 40.2 g of powder. The molecular weight determined by GPC was 1,000,000 in weight average molecular weight. This powder was designated as Polymer A-1. The IR, NMR, and elemental analysis data are as follows:

IR data: 2964 $cm^{-1}$ (—CH), 1733 $cm^{-1}$ (O—C=O), 1651 $cm^{-1}$ (N—C=O), 1458 $cm^{-1}$ (—CH), 1253 $cm^{-1}$ (P=O), 1168 $cm^{-1}$ (C—O—C), 997 $cm^{-1}$ (P—O—C).

NMR data: 0.8-1.2 ppm ($CH_3$—C—), 1.4 ppm (—$CH_2$—), 3.3 ppm (—$N(CH_3)_3$), 2.8-3.2 ppm (—N—$(CH_3)_2$), 3.7-4.4 ppm (—$CH_2CH_2$—).

Elemental Analysis Data:
Theoretical—C: 53.55%; H: 8.44%; N: 8.74%
Measured—C: 53.40%; H: 8.52%; N: 8.80%

From the results above, obtained Polymer A-1 was found to be a polymer having the chemical structure obtained by copolymerization of 50 mol % MPC, 5 mol % SMA, and 45 mol % DMAA.

Synthesis Example 1-2

Polymer A-2; MPC 0.30—SMA 0.03—DMAA 0.67

24.13 g of MPC, 2.77 g of SMA, and 18.11 g of DMAA were dissolved in 55.0 g of n-propanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 42.4 g of powder. The molecular weight determined by GPC was 1,2000,000 in weight average molecular weight. This powder was designated as Polymer A-2. The IR, NMR, and elemental analysis data are as follows:

IR data: 2964 $cm^{-1}$ (—CH), 1733 $cm^{-1}$ (O—C=O), 1651 $cm^{-1}$ (N—C=O), 1458 $cm^{-1}$ (—CH), 1253 $cm^{-1}$ (P=O), 1168 $cm^{-1}$ (C—O—C), 997 $cm^{-1}$ (P—O—C).

NMR data: 0.8-1.2 ppm ($CH_3$—C—), 1.4 ppm (—$CH_2$—), 3.3 ppm (—$N(CH_3)_3$), 2.8-3.2 ppm (—N—$(CH_3)_2$), 3.7-4.4 ppm (—$CH_2CH_2$—).

Elemental Analysis Data:
 Theoretical—C: 56.37%, H: 8.70%; N: 10.90%
 Measured: C: 56.41%; H: 8.69%; N: 10.87%

From the results above, obtained Polymer A-2 was found to be a polymer having the chemical structure obtained by copolymerization of 30 mol % MPC, 3 mol % SMA, and 67 mol % DMAA.

Synthesis Example 1-3

Polymer A-3; MPC 0.70—SMA 0.06—DMAA 0.24

32.96 g of MPC, 3.24 g of SMA, and 3.80 g of DMAA were dissolved in 60.0 g of n-propanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 36.1 g of powder. The molecular weight determined by GPC was 700,000 in weight average molecular weight. This powder was designated as Polymer A-3. The IR, NMR, and elemental analysis data are as follows:
 IR data: 2964 $cm^{-1}$ (—CH), 1733 $cm^{-1}$ (O—C=O), 1651 $cm^{-1}$ (N—C=O), 1458 $cm^{-1}$ (—CH), 1253 $cm^{-1}$ (P=O), 1168 $cm^{-1}$ (C—O—C), 997 $cm^{-1}$ (P—O—C).
 NMR data: 0.8-1.2 ppm ($CH_3$—C—), 1.4 ppm (—$CH_2$—) 3.3 ppm (—$N(CH_3)_3$), 2.8-3.2 ppm (—N—$(CH_3)_2$), 3.7-4.4 ppm (—$CH_2CH_2$—).
Elemental Analysis Data:
 Theoretical—C: 50.55%; H: 8.15%; N: 6.72%
 Measured—C: 50.46%; H: 8.14%; N: 6.72%

From the results above, obtained Polymer A-3 was found to be a polymer having the chemical structure obtained by copolymerization of 70 mol % MPC, 6 mol % SMA, and 24 mol % DMAA.

Synthesis Example 1-4

Polymer A-4; MPC 0.70—VMA70 0.02—DEAA 0.28

33.08 g of MPC, 1.22 g of long chain alkylmethacrylate (trade name BLEMMER VMA-70, manufactured by NOF CORPORATION, C16-C24 alkylmethacrylate mixture, average chain length of alkyl groups: 21, abbreviated as VMA70 hereinbelow), and 5.70 g of N-diethylacrylamide (DEAA) were dissolved in 60.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 35.2 g of powder. The molecular weight determined by GPC was 700,000 in weight average molecular weight. This powder was designated as Polymer A-4. The IR, NMR, and elemental analysis data are as follows:
 IR data: 2972 $cm^{-1}$ (—CH), 1734 $cm^{-1}$ (O—C=O), 1651 $cm^{-1}$ (N—C=O), 1458 $cm^{-1}$ (—CH), 1254 $cm^{-1}$ (P=O), 1169 $cm^{-1}$ (C—O—C), 997 $cm^{-1}$ (P—O—C).
 NMR data: 0.8-1.2 ppm ($CH_3$—C—), 1.4 ppm (—$CH_2$—), 3.7-4.4 Ppm (—$CH_2CH_2$—).
Elemental Analysis Data:
 Theoretical—C: 51.42%; H: 8.02%; N: 7.28%
 Measured—C: 51.40%; H: 8.00%; N: 7.26%

From the results above, obtained Polymer A-4 was found to be a polymer having the chemical structure obtained by copolymerization of 70 mol % MPC, 2 mol % VMA70, and 28 mol % DEAA.

Synthesis Example 1-5

Polymer A-5; MPC 0.50—LMA 0.10—DMAA 0.40

31.23 g of MPC, 5.38 g of laurylmethacrylate (LMA), and 8.39 g of DMAA were dissolved in 55.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 39.9 g of powder. The molecular weight determined by GPC was 1,000,000 in weight average molecular weight. This powder was designated as Polymer A-5. The IR, NMR, and elemental analysis data are as follows:
 IR data: 2964 $cm^{-1}$ (—CH), 1733 $cm^{-1}$ (O—C=O), 1651 $cm^{-1}$ (N—C=O), 1458 $cm^{-1}$ (—CH), 1253 $cm^{-1}$ (P=O), 1168 $cm^{-1}$ (C—O—C), 997 $cm^{-1}$ (P—O—C).
 NMR data: 0.8-1.2 ppm ($CH_3$—C—), 1.4 ppm (—$CH_2$—), 3.3 ppm (—$N(CH_3)_3$), 2.8-3.2 ppm (—N—$(CH_3)_2$), 3.7-4.4 ppm (—$CH_2CH_2$—)
Elemental Analysis Data:
 Theoretical—C: 54.17%; H: 8.55%; N: 8.03%
 Measured—C: 54.12%; H: 8.54%; N: 8.04%
 Kjeldahl nitrogen content: 2.58% (theoretical: 2.66%)

From the results above, obtained Polymer A-5 was found to be a polymer having the chemical structure obtained by copolymerization of 50 mol % MPC, 10 mol % LMA, and 40 mol % DMAA.

Synthesis Example 1-6

Polymer A-6; MPC 0.75—VMA70 0.04—DMAA 0.21

36.03 g of MPC, 2.16 g of VMA70, and 1.81 g of DMAA were dissolved in 60.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 37.0 g of powder. The molecular weight determined by GPC was 700,000 in weight average molecular weight. This powder was designated as Polymer A-6. The IR, NMR, and elemental analysis data are as follows:
 IR data: 2964 $cm^{-1}$ (—CH), 1733 $cm^{-1}$ (O—C=O), 1651 $cm^{-1}$ (N—C=O), 1458 $cm^{-1}$ (—CH), 1253 $cm^{-1}$ (P=O), 1168 $cm^{-1}$ (C—O—C), 997 $cm^{-1}$ (P—O—C).
 NMR data: 0.8-1.2 ppm ($CH_3$—C—), 1.4 ppm (—$CH_2$—), 3.3 ppm (—$N(CH_3)_3$), 3.7-4.4 ppm (—$CH_2CH_2$—).
Elemental Analysis Data:
 Theoretical—C: 47.70%, H: 7.83%; N: 5.50%
 Measured—C: 47.69%; H: 7.84%; N: 5.51%

From the results above, obtained Polymer A-6 was found to be a polymer having the chemical structure obtained by copolymerization of 75 mol % MPC, 4 mol % VMA70, and 21 mol % DMAA.

Synthesis Example 1-7

Polymer A-7; MPC 0.70—SMA 0.03—VMA70 0.03—DMAA 0.24

28.70 g of MPC, 1.41 g of SMA, 1.58 g of VMA70, and 3.31 g of DMAA were dissolved in 65.0 g of n-propanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 30.0 g of powder. The molecular weight determined by GPC was 500,000 in weight average molecular weight. This powder was designated as Polymer A-7. The IR, NMR, and elemental analysis data are as follows:

IR data: 2964 cm$^{-1}$ (—CH), 1733 cm$^{-1}$ (O—C=O), 1651 cm$^{-1}$ (N—C=O), 1458 cm$^{-1}$ (—CH), 1253 cm$^{-1}$ (P=O), 1168 cm$^{-1}$ (C—O—C), 997 cm$^{-1}$ (P—O—C).

NMR data: 0.8-1.2 ppm (CH$_3$—C—), 1.4 ppm (—CH$_2$—), 3.3 ppm (—N(CH$_3$)$_3$), 2.8-3.2 ppm (—N—(CH$_3$)$_2$), 3.7-4.4 ppm (—CH$_2$CH$_2$—).

Elemental Analysis Data:
 Measured—C: 50.58%; H: 8.15%; N: 6.72%
 Theoretical—C: 50.60%; H: 8.16%; N: 6.72%

From the results above, obtained Polymer A-7 was found to be a polymer having the chemical structure obtained by copolymerization of 70 mol % MPC, 3 mol % SMA, 3 mol % VMA70, and 24 mol % DMAA.

Synthesis Example 1-8

Polymer A-8; MPC 0.20—SMA 0.02—DMAA 0.78

18.55 g of MPC, 2.13 g of SMA, and 24.32 g of DMAA were dissolved in 55.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 41.1 g of powder. The molecular weight determined by GPC was 800,000 in weight average molecular weight. This powder was designated as Polymer A-8. The IR, NMR, and elemental analysis data are as follows:

IR data: 2964 cm$^{-1}$ (—CH), 1733 cm$^{-1}$ (O—C=O), 1651 cm$^{-1}$ (N—C=O), 1458 cm$^{-1}$ (—CH), 1253 cm$^{-1}$ (P=O), 1168 cm$^{-1}$ (C—O—C), 997 cm$^{-1}$ (P—O—C).

NMR data: 0.8-1.2 ppm (CH$_3$—C—), 1.4 ppm (—CH$_2$—), 3.3 ppm (—N(CH$_3$)$_3$), 2.8-3.2 ppm (—N—(CH$_3$)$_2$), 3.7-4.4 ppm (—CH$_2$CH$_2$—).

Elemental Analysis Data:
 Theoretical—C: 57.78%; H: 8.83%; N: 11.98%
 Measured—C: 57.79%; H: 8.84%; N: 12.00%

From the results above, obtained Polymer A-8 was found to be a polymer having the chemical structure obtained by copolymerization of 20 mol % MPC, 2 mol % SMA, and 78 mol % DMAA.

Synthesis Example 1-9

Polymer A-9; MPC 0.20—LMA 0.10—DMAA 0.70

15.35 g of MPC, 6.61 g of LMA, and 18.05 g of DMAA were dissolved in 60.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 34.2 g of powder. The molecular weight determined by GPC was 800,000 in weight average molecular weight. This powder was designated as Polymer A-9. The IR, NMR, and elemental analysis data are as follows:

IR data: 2964 cm$^{-1}$ (—CH), 1733 cm$^{-1}$ (O—C=O), 1651 cm$^{-1}$ (N—C=O), 1458 cm$^{-1}$ (—CH), 1253 cm$^{-1}$ (P=O), 1168 cm$^{-1}$ (C—O—C), 997 cm$^{-1}$ (P—O—C).

NMR data: 0.8-1.2 ppm (CH$_3$—C—), 1.4 ppm (—CH$_2$—), 3.3 ppm (—N(CH$_3$)$_3$), 2.8-3.2 ppm (—N—(CH$_3$)$_2$), 3.7-4.4 ppm (—CH$_2$CH$_2$—).

Elemental Analysis Data:
 Theoretical—C: 58.93%; H: 9.04%; N: 10.85%
 Measured—C: 58.92%; H: 9.05%; N: 10.84%

From the results above, obtained Polymer A-9 was found to be a polymer having the chemical structure obtained by copolymerization of 20 mol % MPC, 10 mol % LMA, and 70 mol % DMAA.

The monomers, polymerization initiators, solvents, and others used in Synthesis Examples 1-1 to 1-9 are shown in Tables 1 and 2.

TABLE 1

| | Synth. Ex. 1-1 | | Synth. Ex. 1-2 | | Synth. Ex. 1-3 | | Synth. Ex. 1-4 | | Synth. Ex. 1-5 | | Synth. Ex. 1-6 | |
|---|---|---|---|---|---|---|---|---|---|---|---|---|
| | Polymer No. | | | | | | | | | | | |
| | A-1 | | A-2 | | A-3 | | A4 | | A-5 | | A-6 | |
| | mol % | wt (g) | mol % | wt (g) | mol % | wt (g) | mol % | wt (g) | mol % | wt (g) | mol % | wt (g) |
| MPC (formula (2)) | 50 | 31.75 | 30 | 24.13 | 70 | 32.96 | 70 | 33.08 | 50 | 31.23 | 86 | 36.03 |
| DMAA (formula (3)) | 45 | 9.60 | 67 | 18.11 | 24 | 3.80 | | | 40 | 8.39 | | |
| DEAA (formula (3)) | | | | | | | 28 | 5.70 | | | 10 | 1.81 |
| LMA (formula (4)) | | | | | | | | | 10 | 5.38 | | |
| SMA (formula (4)) | 5 | 3.64 | 3 | 2.77 | 6 | 3.24 | | | | | | |
| VMA-70 (formula (4)) | | | | | | | 2 | 1.22 | | | 4 | 2.16 |
| Total monomers (g) | | 45 | | 45 | | 40 | | 40 | | 45 | | 40 |
| Ethanol (g) | | 55 | | | | | | 60 | | 55 | | 60 |
| n-Propanol (g) | | | | 55 | | 60 | | | | | | |
| PB-ND (g) | | 0.1 | | 0.1 | | 0.1 | | 0.1 | | 0.1 | | 0.1 |

TABLE 1-continued

|  | Synth. Ex. 1-1 | | Synth. Ex. 1-2 | | Synth. Ex. 1-3 | | Synth. Ex. 1-4 | | Synth. Ex. 1-5 | | Synth. Ex. 1-6 | |
|---|---|---|---|---|---|---|---|---|---|---|---|---|
|  | Polymer No. | | | | | | | | | | | |
|  | A-1 | | A-2 | | A-3 | | A4 | | A-5 | | A-6 | |
|  | mol % | wt (g) | mol % | wt (g) | mol % | wt (g) | mol % | wt (g) | mol % | wt (g) | mol % | wt (g) |
| (Monomer of formula (3))/ (Monomer of formula (2)) mol % | 90.0 | | 223.3 | | 34.3 | | 40.0 | | 80.0 | | 11.6 | |
| (Monomer of formula (4))/ (Monomer of formula (2)) mol % | 10.0 | | 10.0 | | 8.6 | | 2.9 | | 20.0 | | 4.7 | |
| Polymer weight average molecular weight | 1000000 | | 1200000 | | 700000 | | 700000 | | 1000000 | | 700000 | |

TABLE 2

|  | Synth. Ex. 1-7 | | Synth. Ex. 1-8 | | Synth. Ex. 1-9 | |
|---|---|---|---|---|---|---|
|  | Polymer No. | | | | | |
|  | A-7 | | A-8 | | A-9 | |
|  | mol % | wt (g) | mol % | wt (g) | mol % | wt (g) |
| MPC (formula (2)) | 70 | 28.70 | 20 | 18.55 | 20 | 15.35 |
| DMAA (formula (3)) | 24 | 3.31 | 78 | 24.32 | 70 | 18.05 |
| DEAA (formula (3)) | | | | | | |
| LMA (formula (4)) | | | | | 10 | 6.61 |
| SMA (formula (4)) | 3 | 1.41 | 2 | 2.13 | | |
| VMA-70 (formula (4)) | 3 | 1.58 | | | | |
| Total monomers (g) | 35 | | 45 | | 40 | |
| Ethanol (g) | | | 55 | | 60 | |
| n-propanol (g) | 65 | | | | | |
| PB-ND (g) | 0.1 | | 0.1 | | 0.1 | |
| (Monomer of formula (3))/ (Monomer of formula (2)) mol % | 34.3 | | 390.0 | | 350.0 | |
| (Monomer of formula (4))/ (Monomer of formula (2)) mol % | 8.6 | | 10.0 | | 50.0 | |
| Polymer weight average molecular weight | 500000 | | 800000 | | 800000 | |

Synthesis Example 2-1

Polymer B-1; MPC 0.90—SMA 0.02—DMAA 0.08

32.90 g of MPC, 0.84 g of SMA, and 1.26 g of DMAA were dissolved in 65.0 g of ethanol, placed in a four-neck flask, and bubbled with nitrogen for 30 minutes. Then 0.10 g of PB-ND was added at 50° C., and polymerized for 8 hours. The resulting polymer solution was added dropwise into 3 liters of diethyl ether under stirring. The resulting precipitate was taken out by filtration, and vacuum-dried at room temperature for 48 hours to obtain 30.3 g of powder. The molecular weight determined by GPC was 500,000 in weight average molecular weight. This powder was designated as Polymer B-1.

Synthesis Examples 2-2 to 2-6

With each monomer, solvent, and polymerization initiator shown in Table 3, each of Polymers B-2 to B-6 was prepared by polymerization in the same way as in Synthesis Example 2-1.

TABLE 3

|  | Synth. Ex. 2-1 | | Synth. Ex. 2-2 | | Synth. Ex. 2-3 | | Synth. Ex. 2-4 | | Synth. Ex. 2-5 | | Synth. Ex. 2-6 | |
|---|---|---|---|---|---|---|---|---|---|---|---|---|
|  | Polymer No. | | | | | | | | | | | |
|  | B-1 | | B-2 | | B-3 | | B-4 | | B-5 | | B-6 | |
|  | mol % | wt (g) | mol % | wt (g) | mol % | wt (g) | mol % | wt (g) | mol % | wt (g) | mol % | wt (g) |
| MPC (formula (2)) | 90 | 32.90 | 54 | 34.58 | 15 | 14.94 | 50 | 27.26 | 90 | 31.04 | 50 | 33.68 |
| DMAA (formula (3)) | | | 45 | 9.68 | 83 | 27.78 | 20 | 3.66 | | | 50 | 11.32 |

TABLE 3-continued

|  | Synth. Ex. 2-1 | | Synth. Ex. 2-2 | | Synth. Ex. 2-3 | | Synth. Ex. 2-4 | | Synth. Ex. 2-5 | | Synth. Ex. 2-6 | |
|---|---|---|---|---|---|---|---|---|---|---|---|---|
|  | \multicolumn{12}{c}{Polymer No.} |
|  | B-1 | | B-2 | | B-3 | | B-4 | | B-5 | | B-6 | |
|  | mol % | wt (g) | mol % | wt (g) | mol % | wt (g) | mol % | wt (g) | mol % | wt (g) | mol % | wt (g) |
| DEAA (formula (3)) | 8 | 1.26 | | | | | | | | | | |
| LMA (formula (4)) | | | | | | | 30 | 14.08 | | | | |
| SMA (formula (4)) | 2 | 0.84 | 1 | 0.74 | 2 | 2.29 | | | 10 | 3.96 | | |
| VMA-70 (formula (4)) | | | | | | | | | | | | |
| Total monomers (g) | 35 | | 45 | | 45 | | 45 | | 35 | | 45 | |
| Ethanol (g) | 65 | | 55 | | | | | | | | 55 | |
| n-Propanol (g) | | | | | 55 | | 55 | | 65 | | | |
| PB-ND (g) | 0.1 | | 0.1 | | 0.1 | | 0.1 | | 0.1 | | 0.1 | |
| (Monomer of formula (3))/(Monomer of formula (2)) mol % | 8.9 | | 83.3 | | 553.3 | | 40.0 | | 0.0 | | 100.0 | |
| (Monomer of formula (4))/(Monomer of formula (2)) mol % | 2.2 | | 1.9 | | 13.3 | | 60.0 | | 11.1 | | 0.0 | |
| Polymer weight average molecular weight | 500000.0 | | 1000000.0 | | 1200000.0 | | 800000.0 | | 500000.0 | | 1000000.0 | |

Example 1-1

In a pressure tight vessel, 0.01 g of Polymer A-1 prepared in Synthesis Example 1-1, 0.05 g of 20 mass % polyhexanide hydrochloride solution, 0.73 g of sodium chloride, 0.10 g of potassium chloride, 0.431 g of sodium phosphate dibasic, 0.033 g of sodium dihydrogen phosphate, and 98.706 g of purified water were introduced, and stirred at 80° C. for 1 hour. After cooled, the resulting mixture was filtered through cellulose acetate (0.2 μm) to obtain contact lens care preparation S-1. The composition is shown in Table 4.

Examples 1-2 to 1-11

With Polymers A-1 to A-9 prepared in Synthesis Examples 1-1 to 1-9, respectively, contact lens care preparations S-2 to S-11, respectively, were prepared in the same way as in Example 1-1. The compositions are shown in Tables 4 and 5.

TABLE 4

|  | No. | | | | | |
|---|---|---|---|---|---|---|
|  | Ex. 1-1 | Ex. 1-2 | Ex. 1-3 | Ex. 1-4 | Ex. 1-5 | Ex. 1-6 |
|  | \multicolumn{6}{c}{Care preparation No.} |
|  | S-1 | S-2 | S-3 | S-4 | S-5 | S-6 |
| Polyhexanide hydrochloride solution | 0.050 | 0.050 | 0.050 | 0.050 | 0.050 | 0.050 |
| Sodium chloride | 0.730 | 0.730 | 0.730 | 0.730 | 0.730 | 0.730 |
| Potassium chloride | 0.100 | 0.100 | 0.100 | 0.100 | 0.100 | 0.100 |
| Sodium phosphate dibasic | 0.431 | 0.431 | 0.431 | 0.431 | 0.431 | 0.431 |
| Sodium dihydrogen phosphate | 0.033 | 0.033 | 0.033 | 0.033 | 0.033 | 0.033 |
| Purified water | 98.706 | 98.706 | 98.706 | 98.706 | 98.706 | 98.706 |
| Polymer A-1 | 0.01 | 0.1 | 2 | — | — | — |
| Polymer A-2 | — | — | — | 0.1 | — | — |
| Polymer A-3 | — | — | — | — | 0.1 | — |
| Polymer A-4 | — | — | — | — | — | 0.1 |

TABLE 5

|  | No. | | | | |
|---|---|---|---|---|---|
|  | Ex. 1-7 | Ex. 1-8 | Ex. 1-9 | Ex. 1-10 | Ex. 1-11 |
|  | \multicolumn{5}{c}{Care preparation No.} |
|  | S-7 | S-8 | S-9 | S-10 | S-11 |
| Polyhexanide hydrochloride solution | 0.050 | 0.050 | 0.050 | 0.050 | 0.050 |
| Sodium chloride | 0.730 | 0.730 | 0.730 | 0.730 | 0.730 |
| Potassium chloride | 0.100 | 0.100 | 0.100 | 0.100 | 0.100 |
| Sodium phosphate dibasic | 0.431 | 0.431 | 0.431 | 0.431 | 0.431 |
| Sodium dihydrogen phosphate | 0.033 | 0.033 | 0.033 | 0.033 | 0.033 |
| Purified water | 98.706 | 98.706 | 98.706 | 98.706 | 98.706 |
| Polymer A-5 | 0.1 | — | — | — | — |
| Polymer A-6 | — | 0.1 | — | — | — |

TABLE 5-continued

| | No. | | | | |
|---|---|---|---|---|---|
| | Ex. 1-7 | Ex. 1-8 | Ex. 1-9 | Ex. 1-10 | Ex. 1-11 |
| | Care preparation No. | | | | |
| | S-7 | S-8 | S-9 | S-10 | S-11 |
| Polymer A-7 | — | — | 0.1 | — | — |
| Polymer A-8 | — | — | — | 0.1 | — |
| Polymer A-9 | — | — | — | — | 0.1 |

Comparative Example 1-1

Contact lens care preparation T-1 was prepared in the same way as in Example 1-1 except that no polymer was used. The composition is shown in Table 6.

Comparative Examples 1-2 to 1-11

Contact lens care preparations T-2 to T-11 were prepared with the compositions shown in Tables 6 and 7 in the same way as in Example 1-1. In the tables, HEC refers to hydroxyethyl cellulose and PVP to polyvinylpyrrolidone.

TABLE 6

| | No. | | | | | |
|---|---|---|---|---|---|---|
| | Comp. Ex. 1-1 | Comp. Ex. 1-2 | Comp. Ex. 1-3 | Comp. Ex. 1-4 | Comp. Ex. 1-5 | Comp. Ex. 1-6 |
| | Care preparation No. | | | | | |
| | T-1 | T-2 | T-3 | T-4 | T-5 | T-6 |
| Polyhexanide hydrochloride solution | 0.050 | 0.050 | 0.050 | 0.050 | 0.050 | 0.050 |
| Sodium chloride | 0.730 | 0.730 | 0.730 | 0.730 | 0.730 | 0.730 |
| Potassium chloride | 0.100 | 0.100 | 0.100 | 0.100 | 0.100 | 0.100 |
| Sodium phosphate dibasic | 0.431 | 0.431 | 0.431 | 0.431 | 0.431 | 0.431 |
| Sodium dihydrogen phosphate | 0.033 | 0.033 | 0.033 | 0.033 | 0.033 | 0.033 |
| Purified water | 98.706 | 98.706 | 98.706 | 98.706 | 98.706 | 98.706 |
| HEC | — | 0.1 | — | — | — | — |
| PVP | — | — | 0.1 | — | — | — |
| Polymer B-1 | — | — | — | 0.1 | — | — |
| Polymer B-2 | — | — | — | — | 0.1 | — |
| Polymer B-3 | — | — | — | — | — | 0.1 |

TABLE 7

| | No. | | | | |
|---|---|---|---|---|---|
| | Comp. Ex. 1-7 | Comp. Ex. 1-8 | Comp. Ex. 1-9 | Comp. Ex. 1-10 | Comp. Ex. 1-11 |
| | Care preparation No. | | | | |
| | T-7 | T-8 | T-9 | T-10 | T-11 |
| Polyhexanide hydrochloride solution | 0.050 | 0.050 | 0.050 | 0.050 | 0.050 |
| Sodium chloride | 0.730 | 0.730 | 0.730 | 0.730 | 0.730 |
| Potassium chloride | 0.100 | 0.100 | 0.100 | 0.100 | 0.100 |
| Sodium phosphate dibasic | 0.431 | 0.431 | 0.431 | 0.431 | 0.431 |
| Sodium dihydrogen phosphate | 0.033 | 0.033 | 0.033 | 0.033 | 0.033 |
| Purified water | 98.706 | 98.706 | 98.706 | 98.706 | 98.706 |
| Polymer B-4 | 0.1 | — | — | — | — |
| Polymer B-5 | — | 0.1 | — | — | — |
| Polymer B-6 | — | — | 0.1 | — | — |
| Polymer A-1 | — | — | — | 3.0 | — |
| Polymer A-8 | — | — | — | — | 3.0 |

Evaluation of Care Preparations Prepared in Examples 1-1 to 1-11

100 ml of one of obtained care preparations S-1 to S-11 was measured out, and the HEMA gel or the silicon hydrogel was soaked overnight in the liquid. The surface friction coefficient and surface hydrophilicity of the soaked gel were measured and evaluated. The results are shown in Tables 8 and 9.

On the other hand, 10 ml of one of care preparations S-1 to S-11 was measured out, and the *Acanthamoeba* adhesion was evaluated using a commercially-available soft contact lens. The results are shown in Tables 10 and 11.

From the results shown in Tables 8 and 9, it was found that the low friction coefficients improved the lubricities on the gel surfaces, compared to the results of care preparation T-1 without a polymer in Comparative Example 1-1. From the results shown in Tables 10 and 11, the ameba adhesion was found to be lower.

TABLE 8

| | | No. | | | | | |
|---|---|---|---|---|---|---|---|
| | | Ex. 1-1 | Ex. 1-2 | Ex. 1-3 | Ex. 1-4 | Ex. 1-5 | Ex. 1-6 |
| | | Solution No. | | | | | |
| | | S-1 | S-2 | S-3 | S-4 | S-5 | S-6 |
| HEMA gel surface friction coefficient | Friction coefficient | 0.290 | 0.169 | 0.127 | 0.161 | 0.172 | 0.192 |
| | Error | 0.023 | 0.002 | 0.002 | 0.003 | 0.002 | 0.002 |
| | Evaluation | A | A | A | A | A | A |
| HEMA gel surface water wettability | Evaluation | A | A | A | A | A | A |
| Silicon gel surface friction coefficient | Friction coefficient | 0.153 | 0.144 | 0.120 | 0.145 | 0.147 | 0.142 |
| | Error | 0.003 | 0.002 | 0.002 | 0.002 | 0.002 | 0.002 |
| | Evaluation | A | A | A | A | A | A |
| Silicon gel surface water wettability | Evaluation | A | A | A | A | A | A |

TABLE 9

| | | No. | | | | |
|---|---|---|---|---|---|---|
| | | Ex. 1-7 | Ex. 1-8 | Ex. 1-9 | Ex. 1-10 | Ex. 1-11 |
| | | Solution No. | | | | |
| | | S-7 | S-8 | S-9 | S-10 | S-11 |
| HEMA gel surface friction coefficient | Friction coefficient | 0.277 | 0.211 | 0.205 | 0.277 | 0.230 |
| | Error | 0.010 | 0.002 | 0.002 | 0.010 | 0.003 |
| | Evaluation | A | A | A | A | A |
| HEMA gel surface water wettability | Evaluation | A | A | A | A | A |
| Silicon gel surface friction coefficient | Friction coefficient | 0.142 | 0.147 | 0.150 | 0.150 | 0.153 |
| | Error | 0.002 | 0.002 | 0.003 | 0.002 | 0.003 |
| | Evaluation | A | A | A | A | A |
| Silicon gel surface water wettability | Evaluation | A | A | A | A | A |

TABLE 10

| | | No. | | | | | |
|---|---|---|---|---|---|---|---|
| | | Ex. 1-1 | Ex. 1-2 | Ex. 1-3 | Ex. 1-4 | Ex. 1-5 | Ex. 1-6 |
| | | Solution No. | | | | | |
| | | S-1 | S-2 | S-3 | S-4 | S-5 | S-6 |
| *Acanthamoeba* adhesion to HEMA lens surface (Condition 1) | Cell adhesion | 22.4 | 19.0 | 16.3 | 21.8 | 14.7 | 22.4 |
| | Error | 7.1 | 6.4 | 6.2 | 7.0 | 6.3 | 8.1 |
| | Evaluation | A | A | A | A | A | A |
| *Acanthamoeba* adhesion to HEMA lens surface (Condition 2) | Cell adhesion | 23.3 | 19.4 | 16.0 | 22.9 | 16.0 | 22.2 |
| | Error | 7.7 | 6.4 | 6.1 | 7.0 | 6.3 | 8.1 |
| | Evaluation | A | A | A | A | A | A |

TABLE 11

| | | \multicolumn{5}{c}{No.} | | | | |
|---|---|---|---|---|---|---|
| | | Ex. 1-7 | Ex. 1-8 | Ex. 1-9 | Ex. 1-10 | Ex. 1-11 |
| | | \multicolumn{5}{c}{Solution No.} | | | | |
| | | S-7 | S-8 | S-9 | S-10 | S-11 |
| *Acanthamoeba* adhesion to HEMA lens surface (Condition 1) | Cell adhesion | 21.5 | 14.2 | 15.4 | 20.7 | 24.1 |
| | Error | 9.4 | 7.0 | 5.9 | 7.0 | 8.9 |
| | Evaluation | A | A | A | A | A |
| *Acanthamoeba* adhesion to HEMA lens surface (Condition 2) | Cell adhesion | 22.5 | 136.0 | 15.3 | 23.4 | 22.1 |
| | Error | 9.4 | 7.0 | 5.9 | 7.0 | 5.9 |
| | Evaluation | A | A | A | A | A |

Evaluation of Care Preparations Prepared in Comparative Examples 1-1 to 1-11

100 ml of one of obtained care preparations T-1 to T-11 was measured out, and the HEMA gel or the silicon hydrogel was soaked overnight in the liquid. The surface friction coefficient and surface hydrophilicity of the soaked gel were measured and evaluated. The results are shown in Tables 12 and 13. On the other hand, 10 ml of one of care preparations T-1 to T-11 was measured out, and the *Acanthamoeba* adhesion was evaluated using a commercially-available soft contact lens. The results are shown in Tables 14 and 15.

TABLE 12

| | | \multicolumn{6}{c}{No.} | | | | | |
|---|---|---|---|---|---|---|---|
| | | Comp. Ex. 1-1 | Comp. Ex. 1-2 | Comp. Ex. 1-3 | Comp. Ex. 1-4 | Comp. Ex. 1-5 | Comp. Ex. 1-6 |
| | | \multicolumn{6}{c}{Solution No.} | | | | | |
| | | None | T-1 | T-2 | T-3 | T-4 | T-5 |
| HEMA gel surface friction coefficient | Friction coefficient | 3.025 | 2.971 | 3.083 | 1.522 | 1.944 | 0.903 |
| | Error | 0.448 | 0.404 | 0.510 | 0.242 | 0.301 | 0.187 |
| | Evaluation | C | C | C | C | C | B |
| HEMA gel surface water wettability | Evaluation | C | C | C | C | C | B |
| Silicon gel surface friction coefficient | Friction coefficient | 1.570 | 1.582 | 1.552 | 0.764 | 1.016 | 0.403 |
| | Error | 0.130 | 0.136 | 0.154 | 0.047 | 0.087 | 0.050 |
| | Evaluation | C | C | C | C | C | B |
| Silicon gel surface water wettability | Evaluation | C | C | C | C | C | C |

TABLE 13

| | | \multicolumn{5}{c}{No.} | | | | |
|---|---|---|---|---|---|---|
| | | Comp. Ex. 1-7 | Comp. Ex. 1-8 | Comp. Ex. 1-9 | Comp. Ex. 1-10 | Comp. Ex. 1-11 |
| | | \multicolumn{5}{c}{Solution No.} | | | | |
| | | T-6 | T-7 | T-8 | T-9 | T-10 |
| HEMA gel surface friction coefficient | Friction coefficient | Not evaluated due to water insolubility of | 1.120 | 2.988 | Not evaluated due to gel state of care preparation | Not evaluated due to gel state of care preparation |
| | Error | | 0.195 | 0.457 | | |
| | Evaluation | | C | C | | |
| HEMA gel surface water wettability | Evaluation | | C | C | | |

TABLE 13-continued

| | | No. | | | | |
|---|---|---|---|---|---|---|
| | | Comp. Ex. 1-7 | Comp. Ex. 1-8 | Comp. Ex. 1-9 | Comp. Ex. 1-10 | Comp. Ex. 1-11 |
| | | | | Solution No. | | |
| | | T-6 | T-7 | T-8 | T-9 | T-10 |
| Silicon gel surface friction coefficient | Friction coefficient | polymer | 0.466 | 1.534 | | |
| | Error | | 0.048 | 0.132 | | |
| | Evaluation | | B | C | | |
| Silicon gel surface water wettability | Evaluation | | C | C | | |

TABLE 14

| | | No. | | | | | |
|---|---|---|---|---|---|---|---|
| | | Comp. Ex. 1-1 | Comp. Ex. 1-2 | Comp. Ex. 1-3 | Comp. Ex. 1-4 | Comp. Ex. 1-5 | Comp. Ex. 1-6 |
| | | | | Solution No. | | | |
| | | None | T-1 | T-2 | T-3 | T-4 | T-5 |
| *Acanthamoeba* adhesion to HEMA lens surface (Condition 1) | Cell adhesion | 100.0 | 95.2 | 104.1 | 45.2 | 73.2 | 82.0 |
| | Error | 25.4 | 26.0 | 27.7 | 28.0 | 10.9 | 19.4 |
| | Evaluation | C | C | C | B | B | C |
| *Acanthamoeba* adhesion to HEMA lens surface (Condition 2) | Cell adhesion | — | — | — | 49.3 | 80.5 | — |
| | Error | — | — | — | 14.5 | 14.5 | — |
| | Evaluation | — | — | — | B | C | — |

TABLE 15

| | | No. | | | | |
|---|---|---|---|---|---|---|
| | | Comp. Ex. 1-7 | Comp. Ex. 1-8 | Comp. Ex. 1-9 | Comp. Ex. 1-10 | Comp. Ex. 1-11 |
| | | | | Solution No. | | |
| | | T-6 | T-7 | T-8 | T-9 | T-10 |
| *Acanthamoeba* adhesion to HEMA lens surface (Condition 1) | Cell adhesion | Incapable of evaluation due to water insolubility | 32.7 | 104.0 | Not evaluated due to gel state of care preparation | Not evaluated due to gel state of care preparation |
| | Error | | 6.3 | 25.3 | | |
| | Evaluation | | A | C | | |
| *Acanthamoeba* adhesion to HEMA lens surface (Condition 2) | Cell adhesion | | 53.7 | — | | |
| | Error | | 16.9 | — | | |
| | Evaluation | | C | — | | |

Example 2-1

1 g of Polymer A-1 prepared in Synthesis Example 1-1 was measured out, and dissolved in 499 g of ISO saline by stirring at 80° C. for 1 hour. The resulting solution was filtered through a cellulose acetate membrane filter (0.2 μm) to obtain packaging solution U-1.

Examples 2-2 to 2-9

Packaging solutions U-2 to U-9 were prepared in the same way as in Example 2-1 using Polymers A-2 to A-9, respectively, prepared in Synthesis Examples 1-2 to 1-9, respectively.

Evaluation of Packaging Solutions Prepared in Examples 2-1 to 2-9

Into a 110 cc screw tube, 100 ml of one of packaging solutions U-1 to U-9 prepared in Examples 2-1 to 2-9, respectively, was measured out, and the HEMA gel or the silicon hydrogel was soaked in the solution. The surface friction coefficient and surface hydrophilicity of the soaked gel were evaluated. The results are shown in Tables 16 and 17.

On the other hand, 10 ml of one of packaging solutions U-1 to U-9 was measured out, and a commercially-available soft contact lens, SEED 1DAY FINE (trade name, manufactured by SEED CO., LTD.), which had been washed with sterilized ISO saline, was soaked in the solution, and then autoclaved at 121° C. The *Acanthamoeba* adhesion of the soft contact lens treated with one of packaging solution U-1 to U-9 was evaluated. The results are shown in Tables 18 and 19.

From Tables 16 and 17, packaging solutions U-1 to U-9 were found to have significantly lower friction coefficients, compared to the solution of Comparative Example 2-1 without a polymer. From Tables 18 and 19, the ameba adhesions were found to be lower, compared to Comparative Example 2-1, wherein evaluation was made with ISO saline.

TABLE 16

| | | Ex. 2-1 | Ex. 2-2 | Ex. 2-3 | Ex. 2-4 | Ex. 2-5 | Ex. 2-6 |
|---|---|---|---|---|---|---|---|
| | | \multicolumn{6}{c}{Polymer No.} |
| | | A-1 | A-2 | A-3 | A-4 | A-5 | A-6 |
| | | \multicolumn{6}{c}{Packaging solution No.} |
| | | U-1 | U-2 | U-3 | U-4 | U-5 | U-6 |
| HEMA gel surface friction coefficient | Friction coefficient | 0.159 | 0.155 | 0.167 | 0.192 | 0.272 | 0.205 |
| | Error | 0.002 | 0.002 | 0.002 | 0.003 | 0.008 | 0.002 |
| | Evaluation | A | A | A | A | A | A |
| HEMA gel surface water wettability | Evaluation | A | A | A | A | A | A |
| Silicon gel surface friction coefficient | Friction coefficient | 0.140 | 0.140 | 0.141 | 0.139 | 0.136 | 0.146 |
| | Error | 0.002 | 0.002 | 0.002 | 0.002 | 0.002 | 0.002 |
| | Evaluation | A | A | A | A | A | A |
| Silicon gel surface water wettability | Evaluation | A | A | A | A | A | A |

TABLE 17

| | | Ex. 2-7 | Ex. 2-8 | Ex. 2-9 |
|---|---|---|---|---|
| | | \multicolumn{3}{c}{Polymer No.} |
| | | A-7 | A-8 | A-9 |
| | | \multicolumn{3}{c}{Packaging solution No.} |
| | | U-7 | U-8 | U-9 |
| HEMA gel surface friction coefficient | Friction coefficient | 0.200 | 0.262 | 0.223 |
| | Error | 0.002 | 0.003 | 0.004 |
| | Evaluation | A | A | A |
| HEMA gel surface water wettability | Evaluation | A | A | A |
| Silicon gel surface friction coefficient | Friction coefficient | 0.144 | 0.147 | 0.150 |
| | Error | 0.002 | 0.002 | 0.002 |
| | Evaluation | A | A | A |
| Silicon gel surface water wettability | Evaluation | A | A | A |

TABLE 18

| | | Ex. 2-1 | Ex. 2-2 | Ex. 2-3 | Ex. 2-4 | Ex. 2-5 | Ex. 2-6 |
|---|---|---|---|---|---|---|---|
| | | \multicolumn{6}{c}{Polymer No.} |
| | | A-1 | A-2 | A-3 | A-4 | A-5 | A-6 |
| | | \multicolumn{6}{c}{Packaging solution No.} |
| | | U-1 | U-2 | U-3 | U-4 | U-5 | U-6 |
| *Acanthamoeba* adhesion to HEMA lens surface (Condition 1) | Cell adhesion | 20.4 | 21.2 | 15.6 | 23.5 | 20.9 | 14.4 |
| | Error | 6.5 | 8.4 | 5.7 | 7.6 | 7.1 | 6.4 |
| | Evaluation | A | A | A | A | A | A |
| *Acanthamoeba* adhesion to HEMA lens surface (Condition 2) | Cell adhesion | 19.5 | 21.5 | 17.1 | 22.1 | 22.0 | 14.2 |
| | Error | 6.5 | 6.7 | 6 | 8.7 | 7.4 | 6.8 |
| | Evaluation | A | A | A | A | A | A |

TABLE 19

| | | Ex. 2-7 | Ex. 2-8 | Ex. 2-9 |
|---|---|---|---|---|
| | | \multicolumn{3}{c}{Polymer No.} |
| | | A-7 | A-8 | A-9 |
| | | \multicolumn{3}{c}{Packaging solution No.} |
| | | U-7 | U-8 | U-9 |
| *Acanthamoeba* adhesion to HEMA lens surface (Condition 1) | Cell adhesion | 14.6 | 21.8 | 21.0 |
| | Error | 5.5 | 6.2 | 6.4 |
| | Evaluation | A | A | A |
| *Acanthamoeba* adhesion to HEMA lens surface (Condition 2) | Cell adhesion | 16.9 | 22.7 | 21.8 |
| | Error | 6.3 | 6.4 | 5.9 |
| | Evaluation | A | A | A |

Comparative Example 2-1

As a packaging solution without a polymer, ISO saline was used. This is designated as packaging solution V-1.

Comparative Examples 2-2 to 2-7

Packaging solutions V-2 to V-7 were prepared by dissolving Polymers B-1 to B-6 prepared in Synthesis Examples 2-1 to 2-6, respectively, in the ISO saline in the same way as in Example 2-1.

Evaluation of Packaging Solutions Prepared in Comparative Examples 2-1 to 2-7

The HEMA gel or the silicon hydrogel was soaked in one of packaging solutions V-1 to V-7 in the same way as in Examples 1-1 to 1-9. The surface friction coefficient and surface hydrophilicity of the soaked gel were evaluated. The results are shown in Table 20.

Further, the ability to inhibit *Acanthamoeba* adhesion was evaluated by the same treatment as in Examples 2-1 to 2-9. The results are shown in Table 21.

What is claimed is:

1. A contact lens care preparation comprising 0.01 to 2 weight/volume % of a polymer having structural units represented by formulae (1a) to (1c):

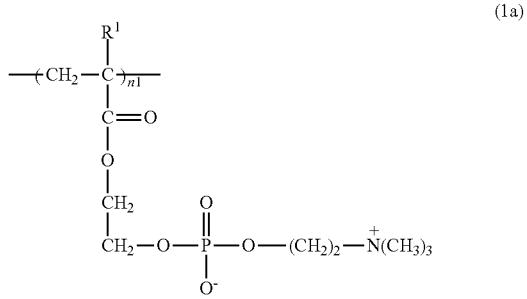

(1a)

TABLE 20

| | | Comp. Ex. 2-1 | Comp. Ex. 2-2 | Comp. Ex. 2-3 | Comp. Ex. 2-4 | Comp. Ex. 2-5 | Comp. Ex. 2-6 | Comp. Ex. 2-7 |
|---|---|---|---|---|---|---|---|---|
| | | | | | Polymer No. | | | |
| | | — | B-1 | B-2 | B-3 | B-4 | B-5 | B-6 |
| | | | | | Packaging solution No. | | | |
| | | V-1 | V-2 | V-3 | V-4 | V-5 | V-6 | V-7 |
| HEMA gel surface friction coefficient | Friction coefficient | 3.068 | 1.383 | 1.749 | 0.811 | Incapable of evaluation due to water insolubility of polymer | 1.012 | 2.979 |
| | Error | 0.425 | 0.233 | 0.228 | 0.174 | | 0.145 | 0.463 |
| | Evaluation | C | C | C | B | | C | C |
| HEMA gel surface water wettability | Evaluation | C | C | C | B | | C | C |
| Silicon gel surface friction coefficient | Friction coefficient | 1.538 | 0.712 | 0.935 | 0.403 | | 0.351 | 1.502 |
| | Error | 0.124 | 0.040 | 0.082 | 0.051 | | 0.049 | 0.113 |
| | Evaluation | C | C | B | B | | B | C |
| Silicon gel surface water wettability | Evaluation | C | C | B | B | | B | C |

TABLE 21

| | | Comp. Ex. 2-1 | Comp. Ex. 2-2 | Comp. Ex. 2-3 | Comp. Ex. 2-4 | Comp. Ex. 2-5 | Comp. Ex. 2-6 | Comp. Ex. 2-7 |
|---|---|---|---|---|---|---|---|---|
| | | | | | Polymer No. | | | |
| | | — | B-1 | B-2 | B-3 | B-4 | B-5 | B-6 |
| | | | | | Packaging solution No. | | | |
| | | V-1 | V-2 | V-3 | V-4 | V-5 | V-6 | V-7 |
| *Acanthamoeba* adhesion to HEMA lens surface (Condition 1) | Cell adhesion | 100.0 | 42.8 | 66.8 | 79.4 | Incapable of evaluation due to water insolubility | 31.5 | 100.3 |
| | Error | 21.4 | 11.5 | 15.4 | 17.6 | | 11.2 | 24.7 |
| | Evaluation | C | B | B-2 | C | | A | C |
| *Acanthamoeba* adhesion to HEMA lens surface (Condition 2) | Cell adhesion | — | 52.1 | 76.4 | — | | 49.9 | — |
| | Error | — | 12.6 | 15.3 | — | | 15.9 | — |
| | Evaluation | — | B | C | — | | C | — |

-continued

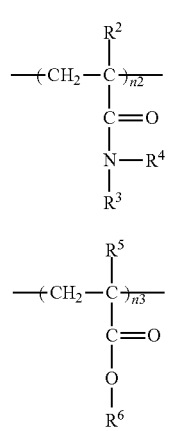

(1b)

(1c)

wherein $R^1$, $R^2$ and $R^5$ are each independently a hydrogen atom or a methyl group; $R^3$ and $R^4$ are each independently a methyl or ethyl group; $R^6$ is a monovalent hydrocarbon group having 12 to 24 carbon atoms; n1, n2, and n3 represent a molar ratio of the structural units (1a), (1b), and (1c), respectively, and fulfill n1:n2:n3=100:10 to 400:2 to 50, and a weight average molecular weight of 5,000 to 2,000,000, wherein said preparation is in a form of a solution.

2. A contact lens packaging solution comprising the contact lens care preparation of claim 1.

* * * * *